United States Patent
Kang et al.

(10) Patent No.: US 11,714,452 B2
(45) Date of Patent: Aug. 1, 2023

(54) FOLDABLE ELECTRONIC DEVICE AND METHOD OF ESTIMATING BIOINFORMATION USING THE SAME

(71) Applicant: SAMSUNG ELECTRONICS CO., LTD., Suwon-si (KR)

(72) Inventors: Jae Min Kang, Seoul (KR); Yong Joo Kwon, Yongin-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/982,061

(22) Filed: Nov. 7, 2022

(65) Prior Publication Data
US 2023/0059810 A1 Feb. 23, 2023

Related U.S. Application Data

(62) Division of application No. 16/854,322, filed on Apr. 21, 2020, now Pat. No. 11,520,375.

(30) Foreign Application Priority Data

Sep. 19, 2019 (KR) .......................... 10-2019-0115510

(51) Int. Cl.
  *G06F 1/16* (2006.01)
  *G06V 40/12* (2022.01)
  *A61B 5/00* (2006.01)

(52) U.S. Cl.
  CPC .......... *G06F 1/1616* (2013.01); *A61B 5/6843* (2013.01); *A61B 5/6898* (2013.01); *G06F 1/1684* (2013.01); *G06V 40/12* (2022.01)

(58) Field of Classification Search
  CPC ... G06F 1/1616; G06F 1/1684; A61B 5/6843; A61B 5/6898; A61B 5/0077;
  (Continued)

(56) References Cited

U.S. PATENT DOCUMENTS 6,714,814 B2    3/2004  Yamada et al.
8,521,239 B2    8/2013  Hosoi et al.
(Continued)

FOREIGN PATENT DOCUMENTS

EP    2 278 776 A1    1/2011
EP    2 767 232 A1    8/2014
(Continued)

OTHER PUBLICATIONS

Communication dated Mar. 29, 2021 issued by the European Intellectual Property Office in counterpart European Application No. 20191430.6.
(Continued)

*Primary Examiner* — Antonio Xavier
(74) *Attorney, Agent, or Firm* — Sughrue Mion, PLLC

(57) ABSTRACT

Provided are foldable electronic device and method for estimating bio-information by using the same. The foldable electronic device may include: a main body part including a first main body and a second main body that are configured to be folded toward each other or unfolded from each other along a fold line where the first main body and the second main body meet; an image sensor part including a first image sensor and a second image sensor which are disposed at the first main body; and a processor configured to obtain a contact image of an object from the first image sensor disposed at the first main body and obtain an image of a marker that is displayed on the second main body, from the second image sensor disposed at the first main body, when the object is in contact with the first image sensor and the main body part is folded along the fold line, and estimate bio-information based on the contact image of the object and the image of the marker.

4 Claims, 19 Drawing Sheets

(58) Field of Classification Search
CPC . A61B 5/02108; A61B 5/165; A61B 2505/07; A61B 5/02028; A61B 5/02416; A61B 5/02438; A61B 5/706; A61B 5/02007; A61B 5/02125; A61B 5/021; A61B 5/0053; A61B 5/0059; A61B 5/02225; A61B 5/72; A61B 5/7445; G06V 40/12

See application file for complete search history.

(56) References Cited

U.S. PATENT DOCUMENTS

| | | | |
|---|---|---|---|
| 8,526,998 | B2 | 9/2013 | Koide et al. |
| 8,886,263 | B2 | 11/2014 | Hosoi et al. |
| 8,918,149 | B2 | 12/2014 | Hosoi et al. |
| 9,313,306 | B2 | 4/2016 | Hosoi et al. |
| 9,392,097 | B2 | 7/2016 | Hosoi et al. |
| 9,479,624 | B2 | 10/2016 | Hosoi et al. |
| 9,622,710 | B2 | 4/2017 | Banet et al. |
| 9,716,782 | B2 | 7/2017 | Hosoi et al. |
| 9,729,971 | B2 | 8/2017 | Hosoi et al. |
| 9,894,430 | B2 | 2/2018 | Hosoi et al. |
| 9,895,067 | B2 | 2/2018 | Park et al. |
| 9,980,666 | B2 | 5/2018 | Bresch et al. |
| 10,079,925 | B2 | 9/2018 | Hosoi et al. |
| 10,158,947 | B2 | 12/2018 | Hosoi et al. |
| 10,219,752 | B2 | 3/2019 | Kang et al. |
| 10,506,343 | B2 | 12/2019 | Hosoi et al. |
| 10,778,823 | B2 | 9/2020 | Hosoi et al. |
| 10,779,075 | B2 | 9/2020 | Hosoi et al. |
| 10,834,506 | B2 | 11/2020 | Hosoi et al. |
| 2007/0276261 | A1 | 11/2007 | Banet et al. |
| 2011/0065482 | A1* | 3/2011 | Koide ............... H04M 1/21 455/566 |
| 2011/0074716 | A1* | 3/2011 | Ono ............... G06F 1/1626 345/173 |
| 2012/0276958 | A1* | 11/2012 | Inami ............... H04M 1/0241 455/566 |
| 2013/0046159 | A1 | 2/2013 | McCombie et al. |
| 2013/0141373 | A1* | 6/2013 | Takuma ............... G06F 3/04883 345/173 |
| 2013/0242809 | A1 | 9/2013 | Tone et al. |
| 2015/0018660 | A1* | 1/2015 | Thomson ............... A61B 5/332 600/393 |
| 2015/0062078 | A1 | 3/2015 | Christman et al. |
| 2015/0080669 | A1 | 3/2015 | Settels et al. |
| 2015/0130738 | A1* | 5/2015 | Park ............... G06F 3/1423 345/173 |
| 2015/0234507 | A1* | 8/2015 | Chun ............... G06F 3/0416 345/173 |
| 2016/0014308 | A1 | 1/2016 | Yamazaki et al. |
| 2016/0085325 | A1* | 3/2016 | Lee ............... G06F 3/0488 345/173 |
| 2016/0198962 | A1 | 7/2016 | Park et al. |
| 2016/0381014 | A1* | 12/2016 | Kim ............... G06F 1/1616 726/7 |
| 2017/0079591 | A1 | 3/2017 | Gruhlke et al. |
| 2017/0340219 | A1 | 11/2017 | Sullivan et al. |
| 2017/0347893 | A1 | 12/2017 | Osoegawa |
| 2018/0144721 | A1* | 5/2018 | Nemoto ............... G09G 5/38 |
| 2018/0255219 | A1 | 9/2018 | Ramaprakash et al. |
| 2019/0090795 | A1 | 3/2019 | Boller |
| 2019/0104997 | A1* | 4/2019 | Kang ............... G06F 3/044 |

FOREIGN PATENT DOCUMENTS

| | | |
|---|---|---|
| EP | 2 806 654 A1 | 11/2014 |
| EP | 2 982 301 A1 | 2/2016 |
| JP | 2016-158805 A | 9/2016 |
| KR | 10-2016-0086710 A | 7/2016 |
| KR | 10-2017-0006746 A | 1/2017 |
| WO | 2009/123498 A1 | 10/2009 |
| WO | 2018/085631 A1 | 5/2018 |
| WO | 2018/162279 A1 | 9/2018 |

OTHER PUBLICATIONS

Notice of Allowance issued in parent U.S. Appl. No. 16/854,322 dated Aug. 10, 2022.

* cited by examiner

FIG. 4B

| | | | | TA | | | |
|---|---|---|---|---|---|---|---|
| 2 | 4 | 5 | 8 | 8 | 8 | 6 | 1 |
| 3 | 6 | 8 | 9 | 9 | 9 | 8 | 2 |
| 3 | 6 | 8 | 9 | 10 | 10 | 8 | 2 |
| 4 | 7 | 8 | 9 | 10 | 10 | 8 | 2 |
| 4 | 7 | 7 | 8 | 9 | 9 | 8 | 3 |
| 2 | 4 | 5 | 6 | 7 | 7 | 5 | 2 |

FOLDABLE ELECTRONIC DEVICE AND METHOD OF ESTIMATING BIOINFORMATION USING THE SAME

CROSS-REFERENCE TO RELATED APPLICATION(S)

This application is a divisional of U.S. application Ser. No. 16/854,322 filed on Apr. 21, 2020, which claims priority from Korean Patent Application No. 10-2019-0115510, filed on Sep. 19, 2019 in the Korean Intellectual Property Office, the disclosures of which are incorporated herein by reference in their entireties.

BACKGROUND

1. Field

Apparatuses and methods consistent with example embodiments relate to a foldable electronic device and estimating bio-information by using the same.

2. Description of the Related Art

Generally, methods of non-invasively measuring blood pressure include a method of measuring blood pressure with an upper arm cuff and a method of estimating blood pressure without the cuff, for example, based on an optical signal emitted to a subject and then reflected back from the subject.

A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large.

Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

According to an aspect of an example embodiment, there is provided a foldable electronic device, including: a main body part including a first main body and a second main body that are configured to be folded toward each other or unfolded from each other along a fold line where the first main body and the second main body meet; an image sensor part including a first image sensor and a second image sensor which are disposed at the first main body; and a processor configured to obtain a contact image of an object from the first image sensor disposed at the first main body and obtain an image of a marker that is displayed on the second main body, from the second image sensor disposed at the first main body, when the object is in contact with the first image sensor and the main body part is folded along the fold line, and estimate bio-information based on the contact image of the object and the image of the marker.

The image sensor part may be disposed on an inner side of the first main body which is not exposed outside the foldable electronic device when the main body part is folded.

The first image sensor may be configured to obtain the contact image when the object gradually changes contact pressure exerted to the first image sensor while the object is in contact with the first image sensor.

The foldable electronic device may further include a display part, which includes a first display and a second display disposed on an inner side of the first main body and an inner side of the second main body respectively, which are not exposed to outside the foldable electronic device when the main body part is folded.

The first display and the second display may be integrally formed to be foldable.

The processor may be further configured to output the image of the marker to the second display of the second main body.

The second image sensor may be further configured to obtain the image of the marker which is output to the second display while the second main body rotates to press the object which is in contact with the first image sensor.

The processor may be further configured to obtain contact pressure that is exerted by the object to the first image sensor, based on a size change of the marker while the second main body rotates to press the object, or based on a size of the marker at a random time.

The processor may be further configured to output a processing result to the display part.

The processor may be further configured to output a bio-information estimation result to the first display, and output information, used in estimating the bio-information, to the second display.

The processor may be further configured to output a bio-information estimation history to the second display, and in response to a user input for selecting an estimation history of a specific time, and the processor may be further configured to output a bio-information estimation result of the specific time to the first display.

The processor may be further configured to obtain a pulse wave signal based on the contact image, and obtain contact pressure between the object and the first image sensor based on the marker image.

The processor may be further configured to obtain an oscillometric envelope, which represents an amplitude of the pulse wave signal versus the contact pressure, and estimate the bio-information based on the oscillometric envelope.

The bio-information may include one or more of blood pressure, vascular age, arterial stiffness, aortic pressure waveform, vascular compliance, stress index, and fatigue level.

According to an aspect of an example embodiment, there is provided a foldable electronic device, including: a main body part including a first main body and a second main body that are configured to be folded toward each other or unfolded from each other along a fold line where the first main body and the second main body meet; an image sensor disposed at the first main body and configured to obtain a contact image of an object; a display disposed at the main body part, and configured to obtain touch data while the object which is in contact with the image sensor and the second main body rotates to press the object against the image sensor; and a processor configured to estimate bio-information based on the contact image and the touch data.

The processor may be further configured to obtain a pulse wave signal based on the contact image of the object, obtain contact pressure between the object and the image sensor based on the touch data, and estimate the bio-information based on the pulse wave signal and the contact pressure.

The processor may be further configured to obtain an oscillometric envelope, which represents an amplitude of the pulse wave signal versus the contact pressure, and estimate bio-information based on the oscillometric envelope.

By using a predetermined contact pressure conversion model, the processor may be further configured to convert a change in a statistic value of pixel intensities, which are obtained during a predetermined period of time in a predetermined area of the display, or the statistic value of the pixel intensities at a random time, into the contact pressure.

According to an aspect of an example embodiment, there is provided a foldable electronic device, including: a main body part including a first main body and a second main body that are configured to be folded toward each other or unfolded from each other along a fold line where the first main body and the second main body meet; a first image sensor disposed at the first main body and configured to obtain a first contact image from a first object; a second image sensor disposed at the second main body and configured to obtain a second contact image from a second object; and a processor configured to estimate bio-information based on the first contact image and the second contact image.

The first image sensor and the second image sensor may be disposed on an outer side of the first main body and an outer side of the second main body respectively, which are exposed to outside of the foldable electronic device when the main body part is folded.

The first object and the second object may be different portions of a palm. When the main body part is unfolded and placed on the palm, the first image sensor and the second image sensor may be configured to obtain the first contact image and the second contact image from the first object and the second object, respectively.

The first object and the second object are fingers of different hands of a user. When the first object and the second object come into contact with each other while the main body part is unfolded and placed on the palm, the first image sensor and the second image sensor may be configured to obtain the first contact image and the second contact image, respectively.

The processor may be further configured to obtain a first pulse wave signal and a second pulse wave signal based on the first contact image and the second contact image, respectively.

The processor may be further configured to obtain characteristic points, which correspond to each other, from each of the first pulse wave signal and the second pulse wave signal, calculate a Pulse Transit Time (PTT) based on a time difference between the obtained characteristic points, and estimate bio-information based on the calculated PTT.

The processor may be further configured to obtain information of an angle formed between the first main body and the second main body while obtaining the contact image of the object, and estimate the bio-information based on the contact image, the touch data, and the information of the angle.

According to an aspect of an example embodiment, there is provided a method of estimating bio-information by using a foldable electronic device that includes a main body part, the main body part including a first main body and a second main body that are configured to be folded toward each other or unfolded from each other along a fold line where the first main body and the second main body meet, the method including: obtaining a contact image of an object by using a first image sensor disposed at the first main body when the object is in contact with the first image sensor and the main body part is folded along the fold line; obtaining an image of a marker that is displayed on the second main body by using a second image sensor disposed at the first main body when the object is in contact with the first image sensor and the main body part is folded along the fold line; and estimating the bio-information based on the contact image and the marker image.

The method may further include outputting the image of the marker to a display disposed on the second main body of the main body part.

The obtaining the marker image may include, by using the second image sensor, obtaining the image of the marker which is output to the display while the object is in contact with the first image sensor, and the second main body rotates to press the object against the first image sensor.

The estimating the bio-information may include: obtaining a pulse wave signal based on the contact image of the object; obtaining contact pressure based on a size change of the marker while the second main body rotates to press the object, or based on a size of the marker at a random time; and estimating the bio-information based on the pulse wave signal and the contact pressure.

According to an aspect of an example embodiment, there is provided a method of estimating bio-information by using a foldable electronic device that includes a main body part, the main body part including a first main body and a second main body that are configured to be folded toward each other or unfolded from each other along a fold line where the first main body and the second main body meet, the method including: obtaining a contact image of an object by using an image sensor disposed at the first main body; obtaining touch data when the object comes into contact with the image sensor and the second main body rotates to press the object against the image sensor, by using a display disposed on the first main body; and estimating the bio-information based on the contact image and the touch data.

The estimating the bio-information may include: obtaining a pulse wave signal based on the contact image of the object; obtaining contact pressure between the object and the image sensor based on the touch data; and estimate the bio-information based on the pulse wave signal and the contact pressure.

BRIEF DESCRIPTION OF THE DRAWINGS

The above and/or other aspects will be more apparent by describing certain example embodiments, with reference to the accompanying drawings, in which:

FIGS. 4A and 4B are diagrams explaining another example of estimating bio-information;

DETAILED DESCRIPTION

Figure 1A:
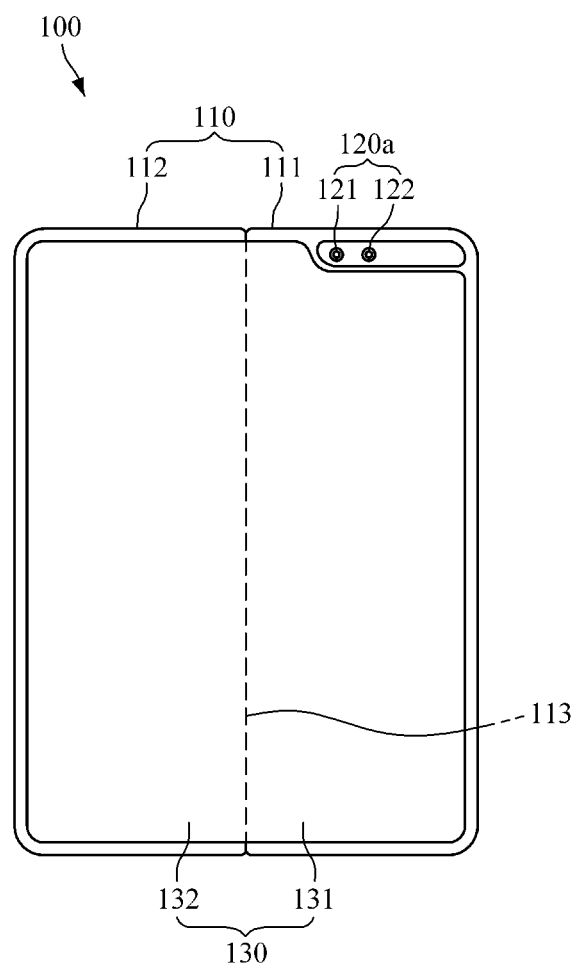
FIGS. 1A to 1C are schematic diagrams illustrating a structure of a foldable electronic device according to an example embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, example embodiments of a foldable electronic device and a method of estimating bio-information using the same will be described in detail with reference to the accompanying drawings.

Figure 1B:
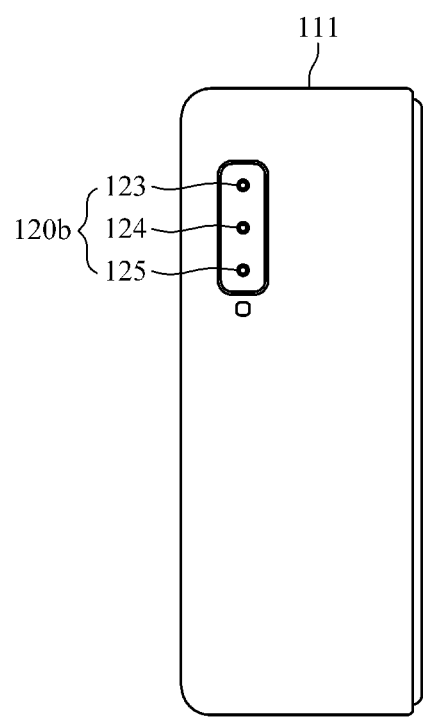
Figure 1C:
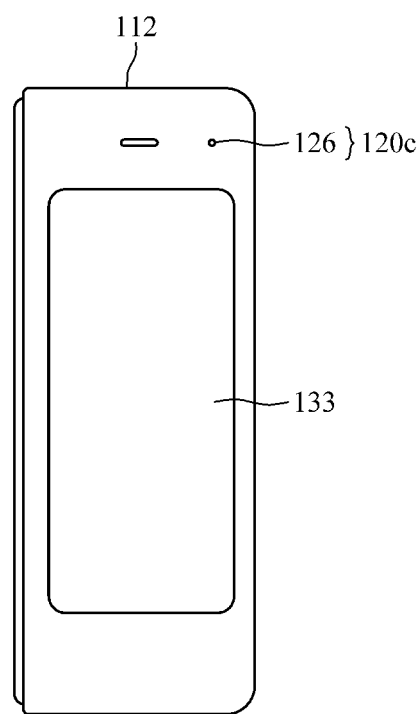

FIGS. 1A to 1C are schematic diagrams illustrating a structure of a foldable electronic device according to an example embodiment.

Referring to FIG. 1A, the foldable electronic device 100 includes a main body part 110 and a display part 130 mounted on the main body part 110.

The main body part 110 includes a first main body 111 and a second main body 112, which are connected to each other by a hinge which is positioned at a rotational axis 113 (e.g., also referred to as a fold axis, a fold line, a hinge axis, or a hinge line). Further, when rotating about the rotational axis, the first main body 111 and the second main body 112 may be transitioned to a folded state to an unfolded state, or vice versa. In this case, when the first main body 110 and the second main body 112 rotate, a surface, on which the display part 130 is disposed (hereinafter referred to as a "display surface" or "front surface"), may be folded inwards. However, the display surface is not limited thereto, and may be folded in an opposite direction.

The display part 130, provided on the display surface of the main body part 110, may include a first display 131, which is disposed on a display surface of the first main body 111, and a second display 132 which is disposed on a display surface of the second main body 112. The first display 131 and the second display 132 may be integrally formed to be foldable as illustrated herein. However, the first display 131 and the second display 132 are not limited thereto, and may be separated from each other. In addition, the first display 131 and the second display 132 may include a touch screen for receiving a user's touch input. Furthermore, the first display 131 and the second display 132 may include a fingerprint sensor for obtaining a fingerprint image when a user touches the sensor with a body part.

In addition, referring to FIG. 1C, the display part 130 may further include a third display 133 disposed on one surface of the main body part 110, which is exposed to the outside when the main body part 110 is folded (hereinafter referred to as a "cover surface" or "rear surface"), i.e., on a cover surface of the second main body 112. The third display 133 may also include a touch screen for receiving a user's touch input. In addition, the third display 133 may further include a fingerprint sensor for obtaining a fingerprint image when a user touches the sensor with a body part. However, the third display 133 is not limited thereto, and may omitted if necessary, or may be manufactured in a compact size without a touch screen, so that only a minimum amount of information may be displayed on the third display 133.

When the main body part 110 is folded, a user may enter commands, such as a request for estimating bio-information, a command for displaying a bio-information estimation history, a command for outputting a health monitoring result, and the like, into the third display 133. Furthermore, when a user unfolds the main body part 110 during an operation for estimating bio-information through the third display 133, information displayed on the third display 133 may be enlarged on the first display 131 and the second display 132.

Moreover, the foldable electronic device 100 may include one or more image sensor parts displayed on the main body part 110. For example, referring to FIGS. 1A and 1B, a first image sensor part 120a and a second image sensor part 120b may be provided respectively on the display surface and the cover surface of the first main body 111. In addition, as illustrated in FIG. 1C, a third image sensor part 120c may be provided on the cover surface of the second main body 112. However, the image sensor parts are not limited thereto, and some of the image sensor parts may be omitted, and another image sensor part may be further provided on the display surface of the second main body 112.

Each of the first, second, and third image sensor parts 120a, 120b, and 120c may include one or more image sensors. For example, as illustrated herein, the first image sensor part 120a, disposed on the display surface of the first main body 111, may include dual image sensors 121 and 122; and the second image sensor part 120b, disposed on the cover surface of the first main body 111, may include triple image sensors 123, 124, and 125. Further, the third image sensor part 120c, disposed on the cover surface of the second main body 112, may include one image sensor 126. However, these are merely examples of image sensors, and the number of image sensors included in each image sensor part is not limited to the illustrated embodiments.

The foldable electronic device 100 may include a processor for processing various functions thereof, and various other hardware modules, such as a communication module, a storage module, and the like, which are mounted in the main body part 110. For example, in response to a request for estimating bio-information, the processor may obtain a variety of information by using at least one of the first, second, and third image sensor parts 120a, 120b, and 120c and/or the display part 130, and may estimate bio-information by using the obtained information. In this case, bio-information may include a variety of cardiovascular information, such as blood pressure, vascular age, arterial stiffness, aortic pressure waveform, vascular compliance, stress index, and fatigue level.

Figure 2:
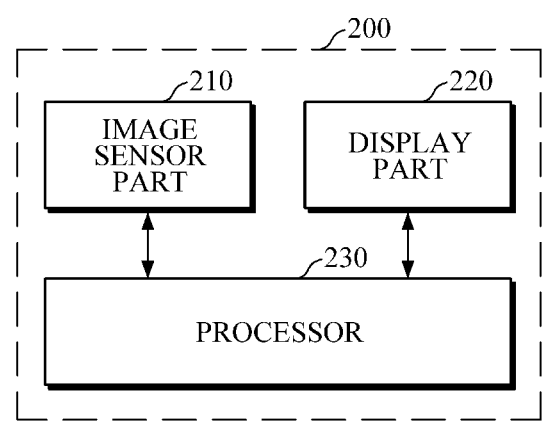
FIG. 2 is a block diagram illustrating a foldable electronic device according to an example embodiment.

FIG. 2 is a block diagram illustrating a foldable electronic device according to an embodiment. FIGS. 3A to 3E are diagrams explaining an example of estimating bio-information.

Referring to FIG. 2, the foldable electronic device 200 according to an embodiment includes an image sensor part 210, a display part 220, and a processor 230.

Upon receiving a request for estimating bio-information, the processor 230 may output a marker M, having a predetermined size, on the second display 132 which is disposed on a display surface of a second main body 202. Further, the processor 230 may control the image sensor 210 to obtain contact image data of an object, and an image of the marker M.

While the object comes into contact with the image sensor part 210 and gradually changes contact pressure, the image sensor part 210 may obtain contact image data of the object. In addition, while obtaining the contact image data, the image sensor part 210 may obtain the image of the marker M output on the display part 220.

Figure 3A:
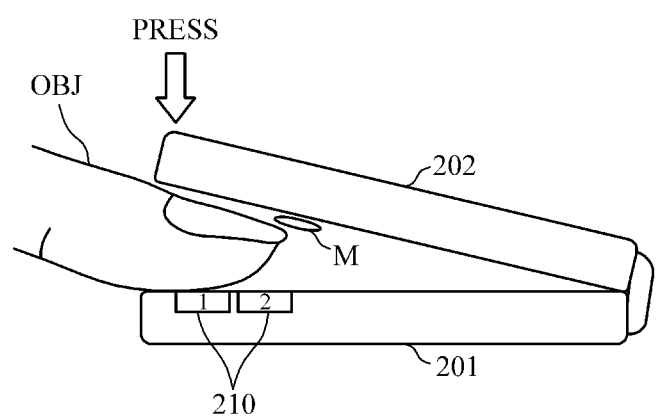
FIGS. 3A to 3E are diagrams explaining an example of estimating bio-information.

For example, referring to FIG. 3A, the image sensor part 210 may be disposed on a display surface of the first main body 201 of the foldable electronic device 200, and may include at least two image sensors 1 and 2. When an object OBJ, e.g., a user's finger, touches the first image sensor 1, the first image sensor 1 may obtain contact image data of the finger.

For example, the first image sensor 1 may detect light scattered or reflected from the object OBJ, and may generate contact image data of the object OBJ. While the object is in contact with the first image sensor 1, the first image sensor 1 may generate continuous image data of the object OBJ.

The first image sensor 1 may be a digital camera sensor or an optical image sensor such as an CMOS Image Sensor (CIS), but is not specifically limited thereto. The first image sensor 1 may include a light source which may emit light onto the object OBJ when the object OBJ touches the first image sensor 1. The light source may include a light emitting diode (LED), a laser diode, and the like, and may be formed as one or an array of a plurality of light sources. However, the light source is not limited thereto, and the first image sensor 1 may use, for example, light emitted from a first display disposed on the display surface of the first main body 201, as a light source for the object OBJ.

Further, the first image sensor 1 may include a pixel array, and each pixel of the pixel array may include a detector such as a photo diode, a photo transistor, and the like. A detector of each pixel may detect light scattered or reflected from the object OBJ, may convert the detected light into an electric signal, and may output pixel data representing a contact image of the object OBJ.

When a user touches the first image sensor 1 with the object OBJ, the user may change contact pressure between the object OBJ and the first image sensor 1. For example, as illustrated herein, when the object OBJ is in contact with the first image sensor 1, the user may gradually apply pressure to the object OBJ by rotating the second main body 202 of the foldable electronic device 200 toward the first main body 201 so that the object OBJ is placed between the first main body 201 and the second main body 202, and the second main body 202 presses the object OBJ against the first main body 201. The first and second main bodies 201 and 202 may be folded to press the object OBJ in a pincer-like manner. However, the change in contact pressure is not limited thereto, and the user may change the contact pressure by pressing the first image sensor 1 with the object OBJ with a gradually increasing force, or by gradually decreasing a pressing force when a force greater than or equal to a predetermined threshold is applied to the first image sensor 1.

When the second main body 202 rotates to press the object OBJ and gradually approaches the second image sensor 2, the second image sensor 2 may obtain an image of a marker M which is output to the second display 132 disposed on the display surface of the second main body 202. In this case, the second image sensor 2 may obtain continuous marker images, starting from an initial state before the second main body 202 is in contact with the object OBJ and applies force thereto to a time when a predetermined force is applied to press the object OBJ.

Figure 3B:
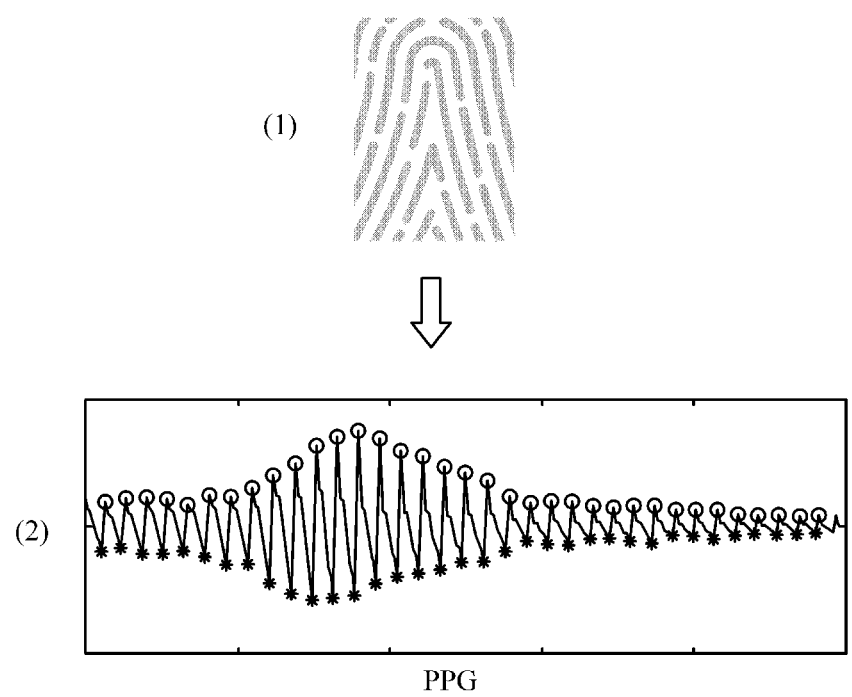

Referring to FIG. 3B, upon receiving pixel data, representing a contact image (1) of the object OBJ, from the first image sensor 1, the processor 230 may obtain a PPG signal based on the received pixel data at each time as illustrated in PPG signal graph (2). In this case, the pixel data at each time may indicate a pixel intensity of each pixel.

For example, the processor 230 may convert the pixel intensity at each time into a pulse wave amplitude at each time by using an amplitude conversion model which represents a correlation between the pixel intensity and the amplitude. For example, the amplitude conversion model may be an equation for calculating an average of the pixel intensities, but is not limited thereto. In addition, the processor 230 may set a region of interest by using the contact image (1) of FIG. 3B, and may obtain an amplitude based on the intensity of pixels in the set region of interest. In this case, the processor 230 may obtain a predetermined region based on a characteristic point, e.g., the center of a fingerprint, as a region of interest from the contact image.

Figure 3C:
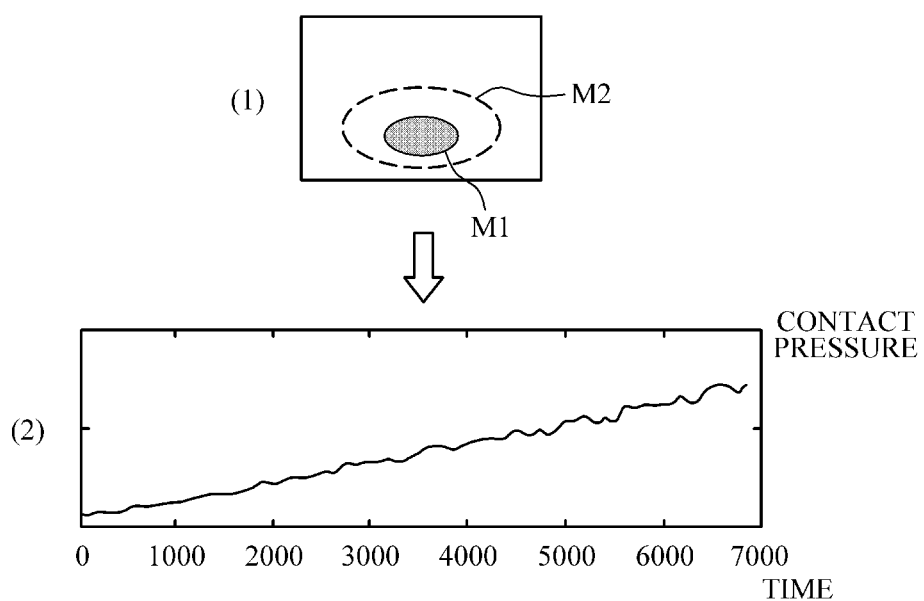

Referring to FIG. 3C, upon receiving a marker image (1) from the second image sensor 2, the processor 230 may obtain contact pressure between the object OBJ and the first image sensor 1 based on the marker image (1) as illustrated in a contract pressure graph (2).

For example, based on marker images received during a predetermined period of time, the processor 230 may obtain a size change of a marker at each time (e.g., see size M1 and size M2 in FIG. 3C), starting from an initial time when the object comes into contact with the first image sensor 1 to a final time. In other words, as force applied by the second main body 202 to the object gradually increases, the marker M output on the second display 132 gradually gets closer to the second image sensor 2, such that the size of the marker image obtained by the second image sensor 2 also gradually increases. Further, by converting the size change of the marker at each time, the processor 230 may obtain contact pressure at each time. For example, the processor 230 may obtain contact pressure by using a contact pressure conversion model which represents a correlation between the size change of the marker and the contact pressure. In this case, the contact pressure conversion model may be a general linear or non-linear estimation equation obtained from a plurality of users. Alternatively, the contact pressure conversion model may be an estimation equation personalized for a specific user by calibration.

In another example, instead of converting the size change of the marker at each time into contact pressure, the processor 230 may obtain contact pressure based on a marker size itself at a random time after a predetermined force is applied, e.g., a final time when a maximum force is applied, or based on a size change of a marker at the final time compared to the initial time.

The processor 230 may estimate bio-information based on the obtained pulse wave signal and contact pressure. For example, based on the pulse wave signal and the contact pressure, the processor 230 may estimate blood pressure using oscillometry.

Figure 3D:
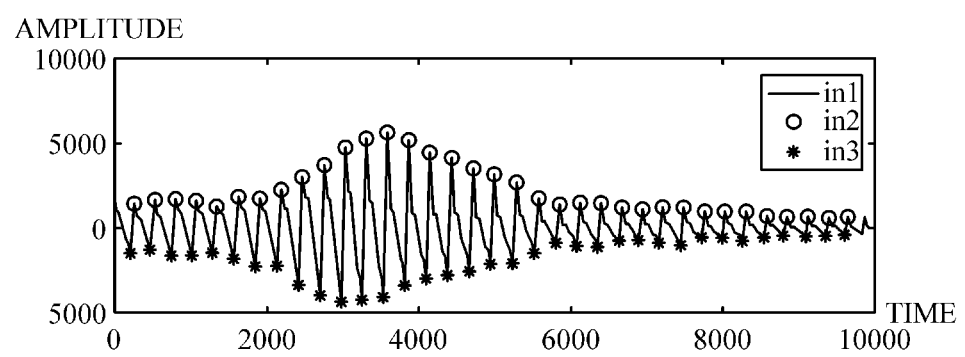
Figure 3E:
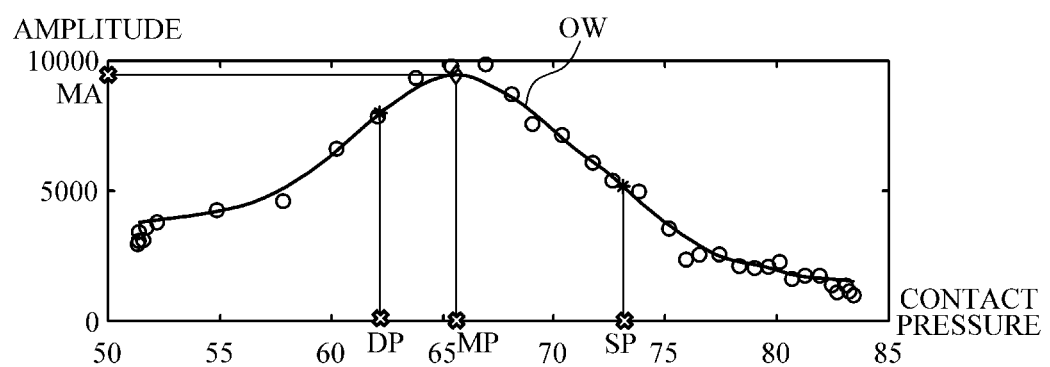

FIGS. 3D and 3E are diagrams illustrating an example of estimating blood pressure using oscillometry.

FIG. 3D is a diagram illustrating an example of a pulse wave signal obtained as described above. As illustrated in FIG. 3D, when a user touches the first image sensor 1 with an object and gradually increases force by pressing the object with the second main body 202, the amplitude of the pulse wave signal (e.g., an intensity of a detected light) also shows a gradually increasing trend during a predetermined period of time. The processor 230 may extract a peak-to-peak point of the pulse wave signal waveform by subtracting a negative (−) amplitude value in3 from a positive (+) amplitude value in2 of a waveform envelope in1 at each measurement time, and may obtain the oscillometric envelope OW by plotting the peak-to-peak amplitude at each measurement time against the contact pressure value at the same point in time, as illustrated in FIG. 3D.

Referring to FIG. 3E, the processor 230 may obtain features for estimating blood pressure from the obtained oscillometric envelope OW. The processor 230 may obtain, as features, an amplitude value MA of a blood pressure signal at a maximum peak point, a contact pressure value MP at the maximum peak point, contact pressure values SP and DP at the left and right points which are distant from the contact pressure value MP at the maximum peak point and which correspond to amplitude values having a preset peak ratio (e.g., 0.5 to 0.7) to the amplitude value MA at the maximum peak point, and the like from the oscillometric envelope OW. However, the features are not limited thereto, and the processor 230 may obtain additional features, such as a maximum amplitude value, a time value corresponding to the maximum amplitude value, time and amplitude values at points related to a propagation wave and a reflection wave, a combination of the obtained values, and the like.

Upon extracting the features, the processor 230 may estimate blood pressure by applying a pre-defined blood pressure estimation model. The blood pressure estimation model may be defined as various linear or non-linear combination functions, such as addition, subtraction, division, multiplication, logarithmic value, regression equation, and the like, with no specific limitation. For example, the following Equation 1 represents a simple linear function.

$$y = ax + b \qquad \text{[Equation 1]}$$

Herein, y denotes an estimated blood pressure value to be obtained; x denotes an extracted feature value; and a and b are values pre-obtained by preprocessing, and may be values personalized for each user. For example, by using the above Equation 1 which is defined for each of mean arterial pressure (MAP), diastolic blood pressure (DBP), and systolic blood pressure (SBP), the processor 230 may independently estimate each blood pressure. For example, by inputting the extracted feature values MP, DP, and SP into the function, which is defined for each of the feature values, the processor 230 may obtain MAP, DBP, and SBP independently.

Figure 4A:
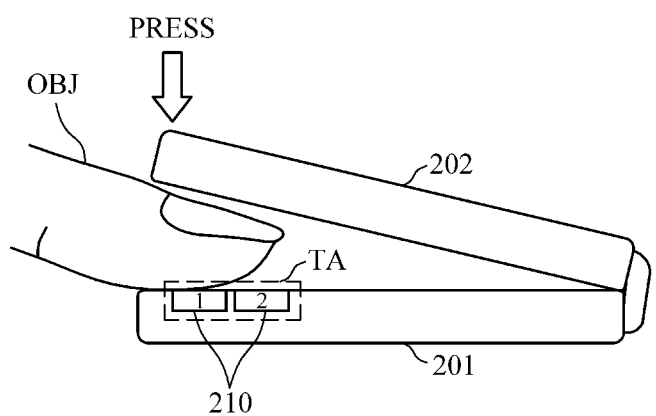

FIGS. 4A and 4B are diagrams explaining another example of estimating bio-information.

Referring to FIGS. 2, 4A and 4B, when a user touches a touch area TA of the first display, provided on the first main body 201, with the object OBJ and rotates the second main body 202 to press the object with a gradually increasing force, the first image sensor 1 and/or the second image sensor 2, disposed in the touch area, may obtain contact image data of the object.

Further, a touch screen of the first display disposed on the first main body 201 may generate touch data in response to contact of the object. In this case, the touch screen includes an optical type panel, a capacitive type panel, a resistive type panel, an InfraRed (IR) type panel, a Surface Acoustic Wave (SAW) type panel, an ElectroMagnetic (EM) type panel, an ElectroMagnetic Resonance (EMR) type panel, and the like.

For example, the touch data may be distribution of pixel intensities, as illustrated in FIG. 4B. In the case where the touch screen panel is a capacitive type panel, the touch data may be distribution of capacitance accumulated in each pixel. In the case where the touch screen panel is an optical type panel, the touch screen may include a light source and a detector, in which the touch data may be distribution of intensities of light detected by each pixel of the detector when light, emitted by the light source, is scattered or reflected from the object OBJ. Generally, when pressure is applied to the touch screen, a contact time and a contact area change as the pressure changes, and the pixel intensity changes accordingly.

As described above, the processor 230 may obtain a pulse wave signal based on the contact image data of the object which are obtained from the first image sensor 1 and/or the second image sensor 2. Further, upon receiving touch data at each time, the processor 230 may obtain contact pressure at each time based on the touch data at each time. For example, the processor 230 may convert a statistic value, such as a sum total, a mean value, a median value, and the like, of the pixel intensities in the touch area TA at each time into a contact pressure value at each time. In this case, a contact pressure conversion model, which represents a correlation between the pixel intensity and the contact pressure may be pre-defined as a linear or non-linear function.

Upon obtaining the pulse wave signal and the contact pressure, the processor 230 may estimate bio-information using oscillometry as described above with reference to FIGS. 3D and 3E. For example, upon obtaining a statistic value of the pixel intensities at each time, the processor 230 may obtain contact pressure based on a change in the statistic value of the pixel intensities at each time compared to the pixel intensity at a random time (e.g., an initial measurement time). However, the processor 230 is not limited thereto, and may obtain contact pressure based on a statistic value at a random time (e.g., a final measurement time).

An example of obtaining contact pressure by using a marker image or touch data is described above with reference to FIGS. 3A to 3C. However, the example of obtaining contact pressure is not limited thereto; and while the second main body 202 is folded to press the object, the processor 230 may obtain contact pressure by measuring an angle formed between the first main body 201 and the second main body 202, and by using an angle change between the initial time and each time.

Referring back to FIG. 2, the processor 230 may output a processing result through the display part 220. For example, the processor 230 may output a bio-information estimation result to the first display 131, and may output information used in estimating bio-information, e.g., the pulse wave signal, the contact pressure, the oscillometric envelope, and the like, to the second display 132. Alternatively, the processor 230 may output a bio-information estimation history to the second display 132; and when a user selects a bio-information estimation history of a specific time, the processor 230 may output a bio-information estimation result of the selected time to the first display 131. In addition, the processor 230 may briefly display an estimated bio-information value and the like to the third display 133, and when a user requests detailed information and unfolds the main body part 110, the processor 230 may output the detailed information to the first display 131 and the second display 132, but is not limited thereto.

Figure 5:
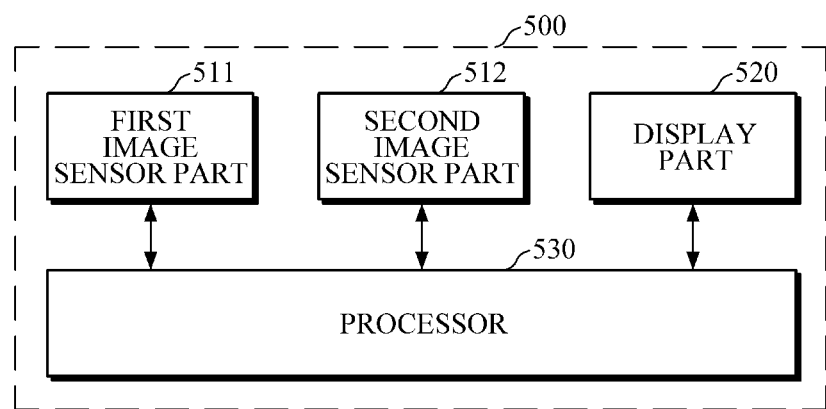
FIG. 5 is a block diagram illustrating a foldable electronic device according to another example embodiment.
Figure 6A:
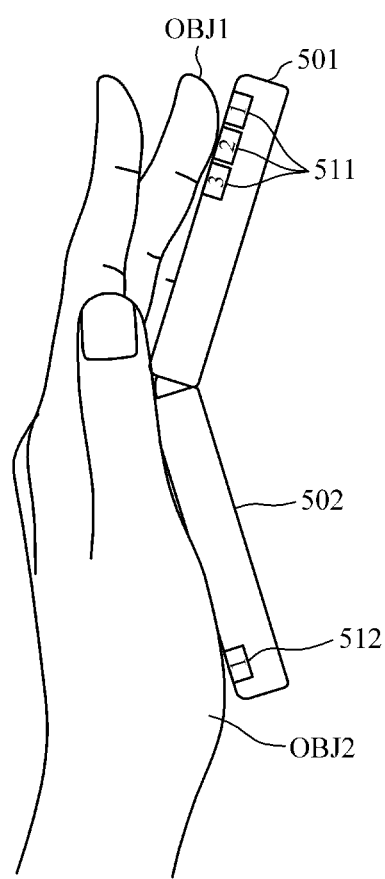
FIGS. 6A to 6C are diagrams explaining yet another example of estimating bio-information.
Figure 6B:
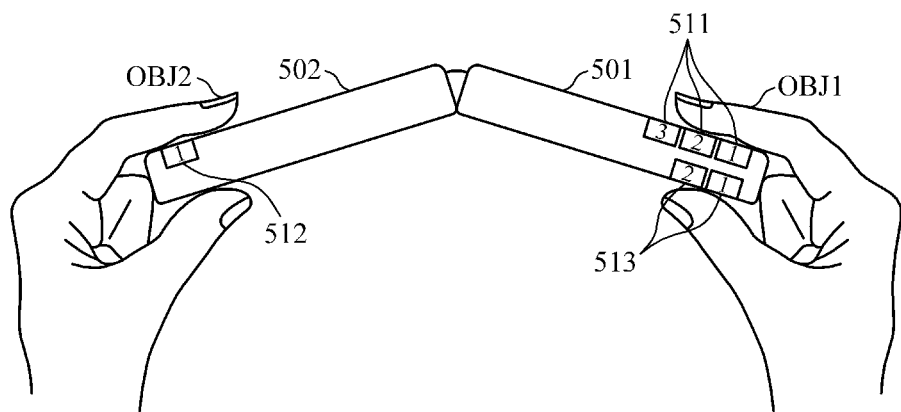
Figure 6C:
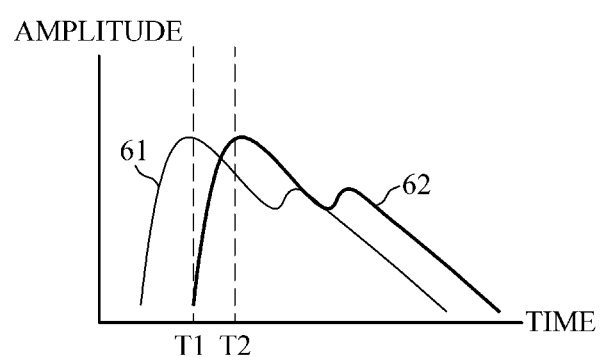

FIG. 5 is a block diagram illustrating a foldable electronic device according to another embodiment. FIGS. 6A to 6C are diagrams explaining yet another example of estimating bio-information.

Referring to FIG. 5, the foldable electronic device 500 according to an embodiment includes a first image sensor part 511, a second image sensor part 512, a display part 520, and a processor 530.

Referring to FIGS. 6A and 6B, the first image sensor part 511 may be disposed on a cover surface of the first main body 501, and the second image sensor part 512 may be disposed on a cover surface of the second main body 502. The first image sensor part 511 may include three image sensors 1, 2, and 3 as illustrated herein. Further, the second image sensor part 512 may include one image sensor 1 as illustrated herein. However, this is merely an example, and the number of the image sensors of each of the image sensor parts 511 and 512 is not specifically limited thereto.

Referring to FIG. 6A, when the first main body 501 and the second main body 420 are unfolded and placed on the palm, the first image sensor part 511 and the second image sensor part 512 may obtain first contact image data and the second contact image data, respectively, from a first object OBJ and a second object OBJ which are in contact with the first image sensor part 511 and the second image sensor part 512 respectively. In this case, the first object OBJ1 may be one end of the palm, e.g., a finger, and the second object OBJ2 may be the other end of the palm, e.g., a portion near the wrist. However, the objects are not limited thereto.

The processor 530 may obtain a first pulse wave signal and a second pulse wave signal based on the first contact image data and the second contact image data which are received from the first image sensor part 511 and the second image sensor part 512 respectively.

As in the case of the first image sensor part 511, if a plurality of image sensors 1, 2, 3 are included, the processor 530 may operate only one of the sensors, and may obtain the first pulse wave signal based on the first contact image data obtained by the image sensor in operation. Alternatively, the processor 530 may operate two or more of the plurality of image sensors 1, 2, and 3, and may obtain the first pulse wave signal by using a plurality of first contact image data obtained from the two or more image sensors. For example, the processor 530 may determine an image sensor at a position, at which a contact state is determined to be relatively good in the plurality of first contact image data, and may obtain the first pulse wave signal by using the first contact image data obtained from the determined image sensor. However, the processor 530 is not limited thereto, and may combine a plurality of first contact image data, and may use the combined result.

Referring to FIG. 6B, while the first main body 501 and the second main body 502 are unfolded, and a user holds the first main body 501 with the thumb and the index finger of the right hand, the user may touch the first image sensor part 511 with the index finger OBJ1 of the right hand. When the user holds the second main body 502 with the thumb and the index finger of the left hand, the user may touch the second image sensor part 512 with the index finger OBJ2 of the left hand. As shown in FIG. 6B, the first image sensor part 511, the second image sensor part 512, and the third image sensor part 513 may be in contact with the right index finger, the left index finger, and the right thumb, respectively. The opposite case in which the user holds the first main body 510 and the second main body 502 with the left hand and the right hand, respectively, is also possible. The first image sensor part 511 and the second image sensor part 512 may obtain the first contact image data and the second contact image data from the first object OBJ1 and the second object OBJ2 which are in contact with the first image sensor part 511 and the second image sensor part 512 respectively.

FIGS. 6A and 6B illustrate an example of obtaining contact image data from two or more objects by using two or more image sensor parts provided for the main body part. However, the example of obtaining contact image data is not limited thereto, and contact image data may be obtained from two or more objects by a combination of the first image sensor part 511 and the third image sensor part 513, or a combination of the second image sensor part 512 and the third image sensor part 513.

The processor 530 may obtain the first pulse wave signal and the second pulse wave signal respectively based on the first contact image data and the second contact image data which are received from the first image sensor part 511 and the second image sensor part 512.

The processor 530 may calculate a Pulse Transit Time (PTT) based on the first pulse wave signal and the second pulse wave signal, which are obtained from different parts of the human body, and may estimate bio-information based on the calculated PTT.

For example, as illustrated in FIG. 6C, the processor 530 may obtain times T1 and T2 of characteristic points, which correspond to each other, from each of a first pulse wave signal 61 and a second pulse wave signal 62, and may calculate a PTT by using a delay time between the obtained characteristic points. In particular, the characteristic point may include a maximum point of a pulse wave, a maximum point of a first-order differential signal, a local minimum point and/or a local maximum point of a second-order differential signal, and the like, but is not limited thereto.

Upon obtaining the PTT, the processor 530 may estimate bio-information by using a pre-defined bio-information estimation model. For example, the bio-information estimation model may be a linear/non-linear function for obtaining an estimated bio-information value by using PTT as a factor. The bio-information estimation model may be defined to further include factors, such as characteristic information including a user's stature, weight, sex, Body Mass Index (BMI), and the like, measurement environment information including measured temperature and humidity, and the like.

In addition to the bio-information, such as blood pressure and the like, by using the PTT, the processor 530 may estimate a health condition according to pulse wave delay of the first pulse wave signal and the second pulse wave signal. For example, if the calculated PTT is greater than or equal to a predetermined threshold, the processor 530 may estimate that there is an abnormality in blood vessels, and may generate health condition information. In this case, the threshold may be set in stages for each of a plurality of intervals, and an abnormality level of health may be set for each stage.

The processor 530 may output a processing result to the display part 520. For example, the processor 230 may provide a user with health-related information, such as a bio-information estimation result, a bio-information estimation history, estimated health condition information, and the like, by properly using the first display, the second display, and the third display.

Figure 7:
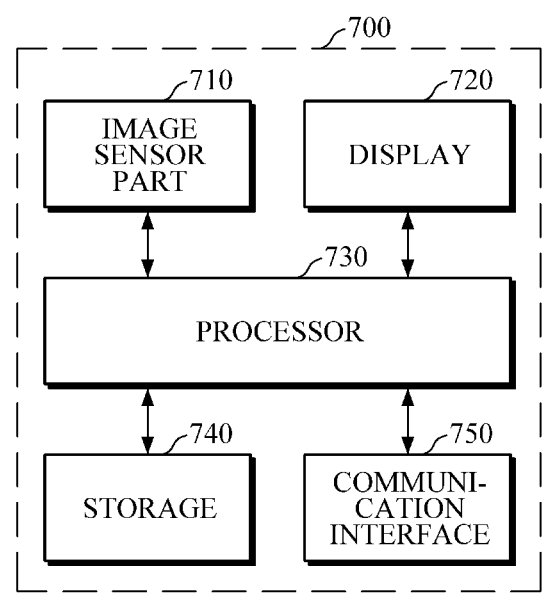
FIG. 7 is a block diagram illustrating a foldable electronic device according to yet another example embodiment.

FIG. 7 is a block diagram illustrating a foldable electronic device according to yet another embodiment.

Referring to FIG. 7, the foldable electronic device 700 includes an image sensor part 710, a display 720, a processor 730, a storage 740, and a communication interface 750. The image sensor part 710, the display 720, and the processor 730 are described above in detail with reference to FIGS. 2 and 5, such that redundant description will be omitted.

The processor 730 may estimate bio-information by using information obtained by the image sensor part 710 and/or the display 720. In this case, the information may include contact image data of an object which are obtained by the image sensor part 710, touch data of the object which are obtained by the display 720, marker images obtained by the image sensor part 710, and the like. Further, when the main body part is folded to press the object while the object is in contact with the image sensor part 710, the information may include an angle, at which the main body part is folded, e.g., an angle formed when the first main body and the second main body are folded.

For example, the processor 730 may estimate bio-information based on oscillometry by using the pulse wave signal, which is obtained based on the contact image data of the object, and the contact pressure which is obtained based on the touch data, the marker image, or the angle data. Alternatively, the processor 730 may calculate a PTT based on a plurality of pulse wave signals, which are obtained by using a plurality of contact image data obtained from two or more objects, and may estimate bio-information by using the PTT.

The storage 740 may store a variety of information related to bio-information, e.g., contact image data, touch data, an angle formed between the first main body and the second main body, a pulse wave signal, contact pressure, a PTT, an estimated bio-information value, monitoring information of a health condition, and the like. Alternatively, the storage 740 may store a variety of reference information required for estimating bio-information. For example, the reference information may include user characteristics information, such as a user's age, sex, stature, weight, health condition, and the like, a bio-information estimation model, an amplitude conversion model, and the like, but is not limited thereto.

In this case, the storage 740 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The communication interface 750 may communicate with an external device by using wired or wireless communication techniques under the control of the processor 730, and may transmit and receive various data to and from the external device. For example, the communication interface 750 may transmit a bio-information estimation result to the external device, and may receive, from the external device, a variety of reference information required for estimating bio-information. In this case, the external device may include a cuff-type blood pressure measuring device, and an information processing device such as a smartphone, a tablet PC, a desktop computer, a laptop computer, and the like.

In this case, examples of the communication techniques may include Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 8:
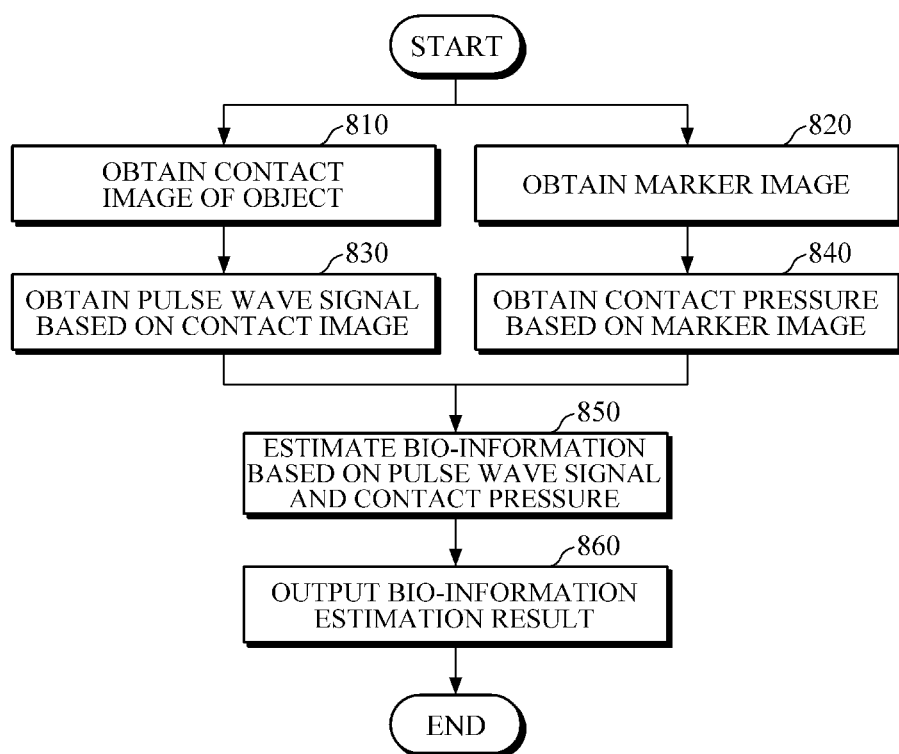
FIG. 8 is a flowchart illustrating a method of estimating bio-information according to an example embodiment.

FIG. 8 is a flowchart illustrating a method of estimating bio-information according to an embodiment. The method of FIG. 8 is an example of the method of estimating bio-information which is performed by the foldable electronic device 200 of FIG. 2, which is described above in detail, and thus will be briefly described below.

The foldable electronic device 200 may obtain contact image data of an object by using a first image sensor disposed at a first main body of the main body part in operation 810. In this case, the first image sensor may be disposed on a display surface of the first main body. In this case, a user may change contact pressure between the object and the first image sensor by pressing the object while rotating the second main body and folding the main body part. The contact image data may be the pixel intensity, i.e., the intensity of light detected by each pixel of a detector of the first image sensor.

Further, while the first image sensor obtains the contact image data from the object, the foldable electronic device 200 may obtain a marker image by using the second image sensor disposed at the first main body in operation 820.

In addition, the foldable electronic device 200 may output a marker on a display, which is disposed on a display surface of the second main body. For example, upon receiving a request for estimating bio-information, the foldable electronic device 200 may output a marker before operation 810. Alternatively, when the user touches the first image sensor with the object, the foldable electronic device 200 may determine whether the object is in contact with the first image sensor; and upon determining that the contact is normally made therebetween, the foldable electronic device 200 may output the marker on the display.

Then, the foldable electronic device 200 may obtain a pulse wave signal in operation 830 based on the contact image data obtained in operation 810. Upon obtaining continuous contact image data, the foldable electronic device 200 may obtain an amplitude of the pulse wave signal at each time based on the pixel intensity at each time.

Subsequently, the foldable electronic device 200 may obtain contact pressure in operation 840 based on the marker image obtained in operation 820. The foldable electronic device 200 may obtain contact pressure based on a size change of the marker at each time compared to an initial time, or based on a marker size at a final time, and the like.

Next, the foldable electronic device 200 may estimate bio-information based on the obtained pulse wave signal and contact pressure in operation 850. For example, the foldable electronic device 200 may obtain an oscillometric envelope based on the pulse wave signal and the contact pressure, and may estimate blood pressure by using the obtained oscillometric envelope.

Then, the foldable electronic device 200 may output a bio-information estimation result in operation 860. The foldable electronic device 200 may output the bio-information estimation result in various manners by properly using a plurality of displays disposed on a display surface of the first main body, a display surface of the second main body, a cover surface of the second main body, and the like. Further, the foldable electronic device 200 may provide a user with the bio-information estimation result, a health condition, and the like by properly using a speaker, a haptic module, and the like by voice, vibrations, tactile sensation, and the like.

Figure 9:
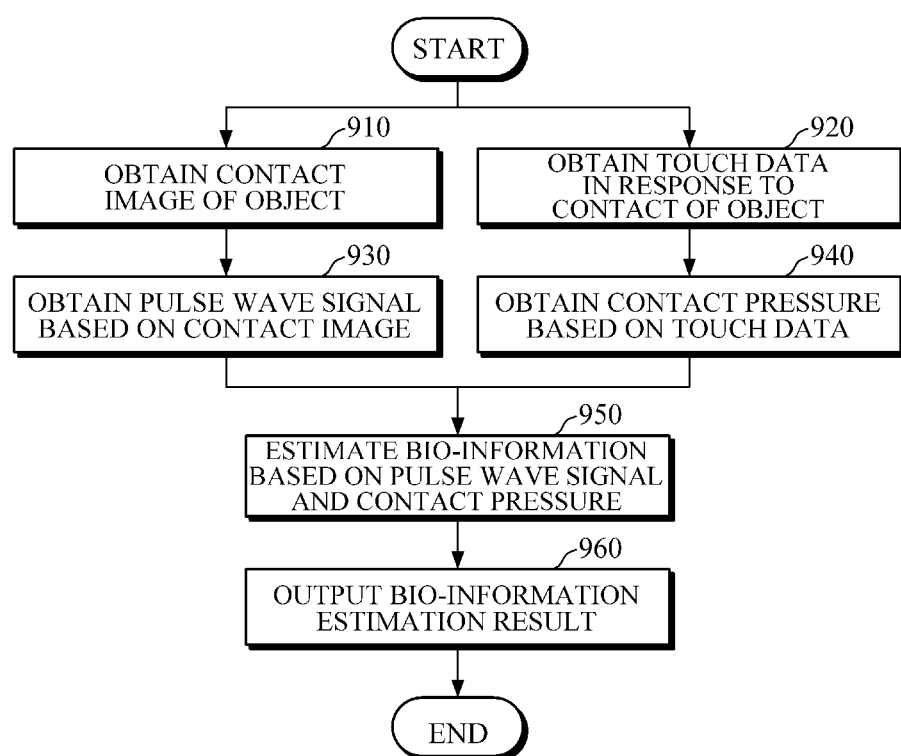
FIG. 9 is a flowchart illustrating a method of estimating bio-information according to another example embodiment.

FIG. 9 is a flowchart illustrating a method of estimating bio-information according to another embodiment. The method of FIG. 9 is an example of the method of estimating bio-information which is performed by the foldable electronic device 200 of FIG. 2, which is described above in detail, and thus will be briefly described below.

The foldable electronic device 200 may obtain contact image data of an object by using a first mage sensor disposed at a first main body of the main body part in operation 910. In this case, the first image sensor may be disposed on a display surface of the first main body. In this case, a user may change contact pressure between the object and the first image sensor by pressing the object while rotating the second main body and folding the main body part.

The foldable electronic device 200 may obtain touch data in operation 920 through a display, disposed on the first main body, in response to contact of the object. In this case, the touch data may be data, such as distribution of capacitance of pixels, intensity of an optical signal, and the like, which are generated according to the type of a touch screen.

Then, the foldable electronic device 200 may obtain a pulse wave signal in operation 930 based on the contact image data obtained in 910.

Subsequently, the foldable electronic device 200 may obtain contact pressure in operation 940 based on the touch data obtained in operation 920. By using a contact pressure conversion model, the foldable electronic device 200 may convert a change in a statistic value of pixel intensities, which are obtained during a predetermined period of time in a touch area of the display, or a statistic value of pixel intensities at a random time into contact pressure.

Next, the foldable electronic device 200 may estimate bio-information based on the obtained pulse wave signal and contact pressure in operation 950. For example, the foldable electronic device 200 may obtain an oscillometric envelope based on the pulse wave signal and the contact pressure, and may estimate blood pressure by using the obtained oscillometric envelope.

Then, the foldable electronic device 200 may output a bio-information estimation result in operation 960. The foldable electronic device 200 may visually output the bio-information estimation result by properly using a plurality of displays, which are disposed on a display surface of the first main body, a display surface of the second main body, a cover surface of the second main body, and the like, a speaker, a haptic module, and the like; and/or the foldable electronic device 200 may provide a user with the bio-information estimation result, a health condition, and the like by using a non-visual method by voice, vibrations, tactile sensation, and the like.

Figure 10:
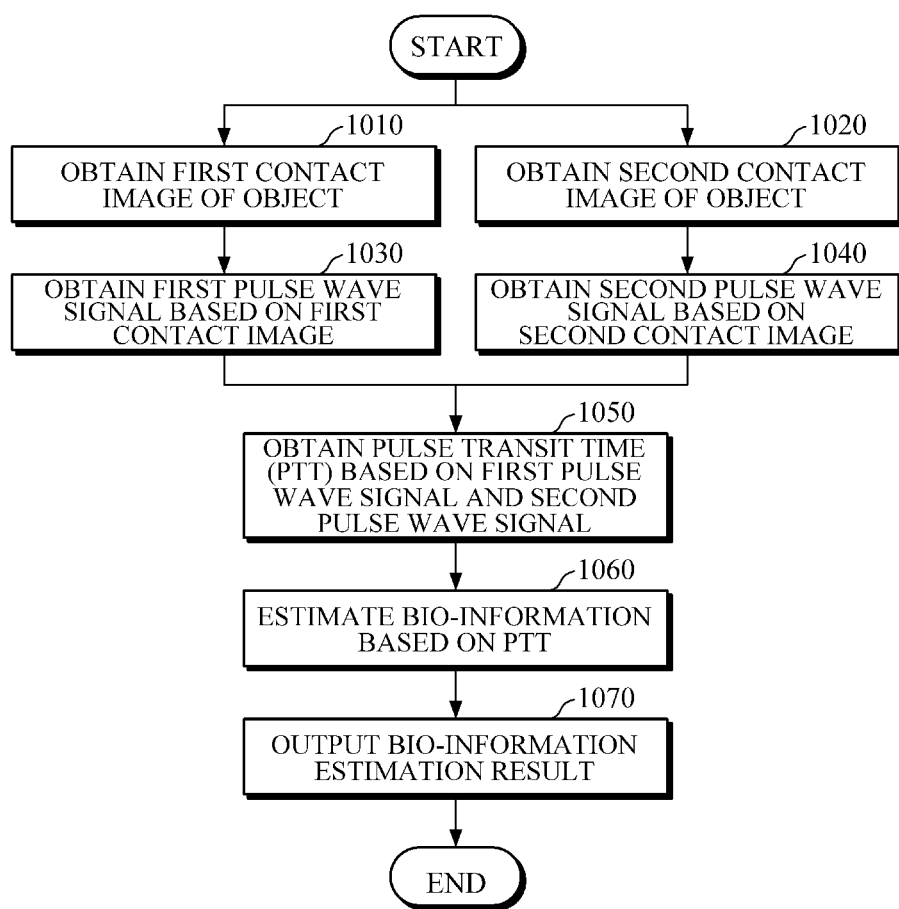
FIG. 10 is a flowchart illustrating a method of estimating bio-information according to yet another example embodiment.

FIG. 10 is a flowchart illustrating a method of estimating bio-information according to yet another embodiment. The method of FIG. 10 is an example of the method of estimating bio-information which is performed by the foldable electronic device 500 of FIG. 5, which is described above in detail, and thus will be briefly described below.

The foldable electronic device 500 may obtain a first contact image data of an object by using a first image sensor disposed on a first main body of the main body part in operation 1010. In this case, the first image sensor may be disposed on a cover surface of the first main body.

Further, the foldable electronic device 500 may obtain a second contact image data of the object by using a second image sensor disposed on a second main body of the main body part in operation 1020.

Then, the foldable electronic device 500 may obtain a first pulse wave signal in operation 1030 based on the first contact image data obtained in operation 1010.

Subsequently, the foldable electronic device 500 may obtain a second pulse wave signal in operation 1040 based on the second contact image data obtained in operation 1020.

Next, the foldable electronic device 500 may obtain a pulse transit time (PTT) based on the obtained first pulse wave signal and second pulse wave signal in operation 1050. For example, the foldable electronic device 500 may obtain, as characteristic points, points corresponding to a maximum point of the pulse wave, a maximum point of a first-order differential signal, a local minimum point/a local maximum point of a second-order differential signal, and the like, and may obtain the PTT based on a time difference between the obtained characteristic points.

Then, the foldable electronic device 500 may estimate bio-information based on the obtained PTT in operation 1060. In this case, the foldable electronic device 500 may estimate bio-information by using a bio-information estimation model which defines a correlation between the PTT and an estimated bio-information value. In addition to the PTT, the bio-information estimation model may further use a user's characteristics, measurement environment information, and the like as additional factors.

Subsequently, the foldable electronic device 500 may output a bio-information estimation result in operation 1070. The foldable electronic device 500 may visually output the bio-information estimation result by properly using a plurality of displays, which are disposed on a display surface of the first main body, a display surface of the second main body, a cover surface of the second main body, and the like, a speaker, a haptic module, and the like; and/or the foldable electronic device 500 may provide a user with the bio-information estimation result, a health condition, and the like by a non-visual method by voice, vibrations, tactile sensation, and the like.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A foldable electronic device comprising:
a main body part including a first main body and a second main body that are configured to be folded toward each other or unfolded from each other along a fold line where the first main body and the second main body meet;
a first image sensor disposed at the first main body and configured to obtain a first contact image from a first object;
a second image sensor disposed at the second main body and configured to obtain a second contact image from a second object; and
a processor configured to estimate bio-information based on the first contact image and the second contact image,
wherein the first object and the second object are different portions of a hand of a user, and
wherein when the main body part is unfolded and placed on the hand, the first image sensor and the second image sensor are configured to obtain the first contact image and the second contact image from the first object and the second object, respectively.

2. The foldable electronic device of claim 1, wherein the first image sensor and the second image sensor are disposed on an outer side of the first main body and an outer side of the second main body, respectively, and the first image sensor and the second image sensor are exposed to outside of the foldable electronic device when the main body part is folded.

3. The foldable electronic device of claim 1, wherein the processor is further configured to obtain a first pulse wave signal and a second pulse wave signal based on the first contact image and the second contact image, respectively.

4. The foldable electronic device of claim 3, wherein the processor is further configured to obtain characteristic points, which correspond to each other, from each of the first pulse wave signal and the second pulse wave signal, calculate a Pulse Transit Time (PTT) based on a time difference between the obtained characteristic points, and estimate bio-information based on the calculated PTT.

* * * * *